US011865249B2

(12) United States Patent
Petit (10) Patent No.: US 11,865,249 B2
(45) Date of Patent: Jan. 9, 2024

(54) DEVICE FOR INHALATION-SYNCHRONISED DISPENSING OF A FLUID PRODUCT

(71) Applicant: APTAR FRANCE SAS, Le Neubourg (FR)

(72) Inventor: Ludovic Petit, Vitot (FR)

(73) Assignee: APTAR FRANCE SAS, Le Neubourg (FR)

(*) Notice: Subject to any disclaimer, the term of this patent is extended or adjusted under 35 U.S.C. 154(b) by 606 days.

(21) Appl. No.: 16/764,089

(22) PCT Filed: Nov. 26, 2018

(86) PCT No.: PCT/FR2018/052979
§ 371 (c)(1),
(2) Date: May 14, 2020

(87) PCT Pub. No.: WO2019/106270
PCT Pub. Date: Jun. 6, 2019

(65) Prior Publication Data
US 2020/0282160 A1    Sep. 10, 2020

(30) Foreign Application Priority Data

Nov. 29, 2017 (FR) .................................. 1761334

(51) Int. Cl.
*A61M 15/00* (2006.01)

(52) U.S. Cl.
CPC ...... *A61M 15/0095* (2014.02); *A61M 15/009* (2013.01); *A61M 15/0021* (2014.02); *A61M 15/0025* (2014.02); *A61M 2205/8281* (2013.01)

(58) Field of Classification Search
CPC .......... A61M 15/0091–0096; A61M 15/0021; A61M 15/009; A61M 15/0025; A61M 2205/8281; A61M 2205/586
(Continued)

(56) References Cited

U.S. PATENT DOCUMENTS 5,060,643 A * 10/1991 Rich ................. A61M 15/0091
128/200.14
5,069,204 A * 12/1991 Smith ............... A61M 15/0091
128/200.23
(Continued)

FOREIGN PATENT DOCUMENTS

FR      2 775 668 A1   9/1999
WO    2004/028608 A1   4/2004
(Continued)

OTHER PUBLICATIONS

International Preliminary Report on Patentability with a Translation of Written Opinion in International Application No. PCT/FR2018/052979, dated Jun. 2, 2020.
(Continued)

*Primary Examiner* — Elliot S Ruddie
(74) *Attorney, Agent, or Firm* — Sughrue Mion, PLLC (57) ABSTRACT

An inhalation-synchronized fluid dispenser device having a body, a reservoir containing a fluid and a propellant gas that slides axially in the body, a metering valve, a blocking element movable and/or deformable between a non-actuation position and an actuation position, and an inhalation-controlled trigger system that moves and/or deforms the blocking element from the non-actuation position towards the actuation position. The device includes an actuator fastened on the reservoir and having a proximal wall fastened on the end of the reservoir, a body that slides axially past the proximal wall, and a spring arranged between the proximal wall and a distal wall of the body, the body sliding
(Continued)

axially past the proximal wall between a rest position and a cocked position in which the spring is compressed, such that on actuation of the trigger system, the compressed spring moves the reservoir so as to actuate the metering valve.

13 Claims, 6 Drawing Sheets

(58) Field of Classification Search
 USPC .................................................. 128/200.23
 See application file for complete search history.

(56) References Cited

U.S. PATENT DOCUMENTS

| 2011/0114089 | A1* | 5/2011 | Andersen | .......... | A61M 15/0081 |
|---|---|---|---|---|---|
| | | | | | 128/200.23 |
| 2019/0134322 | A1* | 5/2019 | Fabien | .............. | A61M 15/0091 |

FOREIGN PATENT DOCUMENTS

| WO | 2009/044172 | A1 | 4/2009 |
|---|---|---|---|
| WO | 2010/003846 | A1 | 1/2010 |
| WO | 2017/178764 | A1 | 10/2017 |
| WO | 2017/178765 | A1 | 10/2017 |
| WO | 2017/178767 | A1 | 10/2017 |
| WO | 2017/178768 | A1 | 10/2017 |

OTHER PUBLICATIONS

International Search Report for PCT/FR2018/052979 dated Mar. 6, 2019 [PCT/ISA/210].

* cited by examiner

DEVICE FOR INHALATION-SYNCHRONISED DISPENSING OF A FLUID PRODUCT

CROSS REFERENCE TO RELATED APPLICATIONS

This application is a National Stage of International Application No. PCT/FR2018/052979 filed Nov. 26, 2018, claiming priority based on French Patent Application No. 1761334 filed Nov. 29, 2017.

The present invention relates to a fluid dispenser device in which dispensing is synchronized with inhaling, and more particularly it relates to an inhaler device of the aerosol type synchronized with inhaling.

Breath actuated inhaler (BAI) devices are well known in the state of the art. The main advantage of this type of device is that the dispensing of fluid is synchronized with the patient inhaling, so as to guarantee that the fluid is properly dispensed into the airways. Thus, in the field of aerosol devices, i.e. devices in which the fluid is dispensed by means of a propellant gas, numerous types of breath actuated inhaler device, have been proposed. However, those devices present the drawback of including a large number of parts, i.e. they are complicated and costly to manufacture and to assemble, which is obviously disadvantageous. It is also difficult to find the right balance between reliable triggering on each inhalation, without the trigger threshold being too high, and a latch that is robust enough to prevent accidental or unwanted actuation. Unfortunately, when the latch releases accidentally, the device is actuated automatically and the dose is dispensed, even when the user does not want it.

Thus, in order to dispense the dose properly, what is more important than actuating the device automatically, is for dispensing to be synchronized with the user inhaling, even if actuation or triggering remains manual.

Documents FR 2 775 668, WO 2017/178764, WO 2017/178765, and WO 2017/178768 describe prior-art devices.

A drawback of those devices resides in the risk of the device jamming if the actuation force of the user is too great, i.e. if the user exerts an axial actuation force on the end wall of the reservoir that is too great.

An object of the present invention is to provide an inhalation-synchronized fluid dispenser device that does not have the above-mentioned drawbacks.

Another object of the present invention is to provide an inhalation-synchronized fluid dispenser device that improves operational reliability by guaranteeing effective actuation on each inhalation, without risk of jamming.

Another object of the present invention is to provide an inhalation-synchronized fluid dispenser device that minimizes the risks of accidental or unwanted actuation.

Another object of the present invention is to provide an inhalation-synchronized fluid dispenser device that does not present a trigger threshold that is too high, thereby making it possible for people who are relatively weak, such as the sick or the elderly, to use the device in safe and reliable manner.

Another object of the present invention is to provide an inhalation-synchronized fluid dispenser device that is simple and inexpensive to manufacture and to assemble.

The present invention thus provides an inhalation-synchronized fluid dispenser device comprising a body provided with a mouthpiece, a fluid reservoir containing a fluid and a propellant gas being mounted to slide axially in said body, a metering valve including a valve member being assembled on said reservoir for selectively dispensing the fluid, said device further comprising:

a blocking element that is movable and/or deformable between a non-actuation position in which said metering valve cannot be actuated, and an actuation position in which said metering valve can be actuated, said blocking element, in its non-actuation position, co-operating firstly with the body and secondly with the reservoir so as to prevent said reservoir from moving axially in the body; and an inhalation-controlled trigger system including an inhalation-sensitive member that is deformable and/or movable under the effect of inhaling, said inhalation-sensitive member, when it is deformed and/or moved, moving and/or deforming said blocking element from its non-actuation position towards its actuation position;

said device including an actuator that is fastened on said reservoir, said actuator comprising a proximal wall that is fastened, in particular force-fitted, on the end of the reservoir, a body that slides axially past said proximal wall, and a spring that is arranged between said proximal wall and a distal wall of said body, said body sliding axially past said proximal well between a rest position and a cocked position in which said spring is compressed, such that on said inhalation-controlled trigger system being actuated, said compressed spring moves said reservoir axially in said body so as to actuate said metering valve.

Advantageously, said blocking element is a blocking ring that is fastened, in particular snap-fastened, on said reservoir, and that includes at least one axial tab, in particular three axial tabs, co-operating with a shoulder that is secured to said body so as to prevent said reservoir from moving axially in said body.

Advantageously, said at least one axial tab is deformable radially outwards so as to pass from the non-actuation position towards the actuation position, a trigger element being provided so as to hold said at least one axial tab in the non-actuation position.

Advantageously, said trigger element is mounted to move between a blocking position in which it blocks said blocking element in its non-actuation position, and a release position in which it does not block said blocking element.

Advantageously, said inhalation-sensitive member of said inhalation-controlled trigger system includes a deformable membrane that defines a deformable air chamber, said deformable membrane being fastened to said trigger element, said deformable membrane being deformed during inhaling, so that it moves said trigger element from its blocking position towards its release position.

Advantageously, said spring is a coil spring.

In a variant, said spring may be a plastics spring.

In a variant, said spring may be a foam element.

Advantageously, said the actuator includes a radial flange that extends radially outwards on either side of said body.

Advantageously, the rest position of said actuator is defined by an axial abutment that is formed between a bottom axial edge of said proximal wall and an inner radial shoulder of said body.

Advantageously, the cocked position of said actuator is defined by an axial abutment that is formed between a bottom axial edge of said body and a top axial edge of an inner sleeve that is secured to said body.

These and other characteristics and advantages appear more clearly from the following detailed description, given by way of non-limiting example, and with reference to the accompanying drawings, in which:

Figure 1:
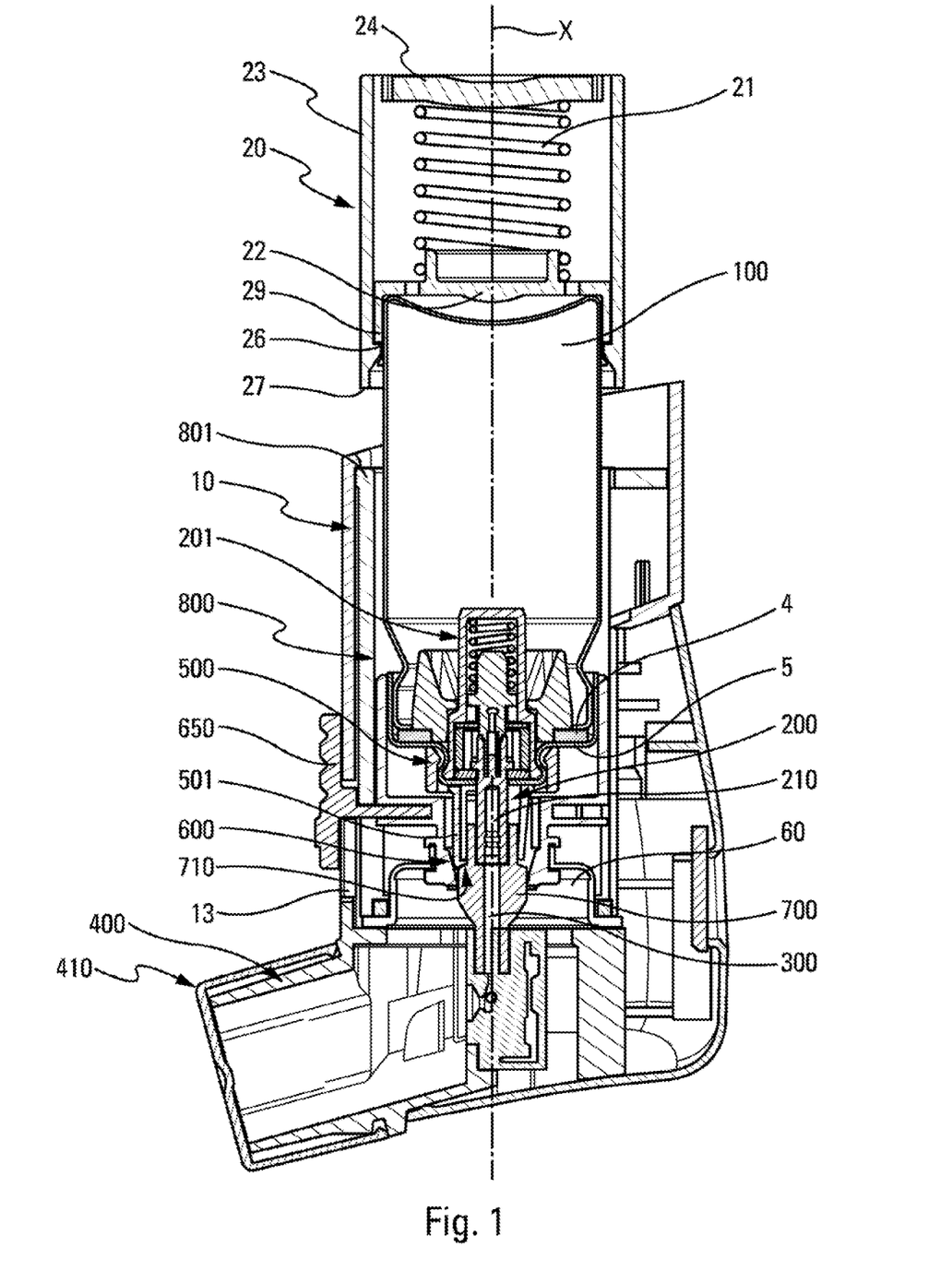
FIG. 1 is a diagrammatic section view of a fluid dispenser device, shown in its rest position.

In the description, the terms "top", "bottom", "upwards", and "downwards" are relative to the position of the device as shown in particular in FIG. 1. The terms "axial" and "radial" are relative to the vertical central axis X shown in particular in FIG. 1. The terms "proximal" and "distal" are relative to the mouthpiece.

The invention applies more particularly to inhaler devices of the aerosol-valve type for oral dispensing, as described in greater detail below, but it could also apply to other types of inhaler device, e.g. of the nasal type.

The figures show an advantageous embodiment of the invention, but naturally one or more of the component parts described below could be made in some other way, while providing functions that are similar or identical.

With reference to the drawings, the device includes a main body 10 provided with a mouthpiece 400. The mouthpiece 400 defines a dispenser orifice through which the user inhales while the device is being used. A removable protective cap 410 may be provided on said mouthpiece 400, in particular while it is being stored, that the user removes before use. FIG. 1 shows such a protective cap that could be of any shape.

An inner sleeve 800 may be provided inside said body 10, as can be seen in the figures.

The body 10 contains a reservoir 100 that contains the fluid to be dispensed and a propellant gas, such as a gas of the hydrofluoroalkane (HFA) type, a metering valve 200 being mounted on said reservoir 100 for selectively dispensing the fluid. The metering valve 200 comprises a valve body 201, and a valve member 210 that, during actuation, is axially movable relative to said valve body 201, and thus relative to said reservoir 100. The metering valve 200 can be of any appropriate type. It may be fastened to the reservoir 100 via a fastener element, preferably a crimped cap 5, preferably with a neck gasket 4 interposed therebetween.

Advantageously, during actuation, the valve member 210 is stationary relative to the body 10, and it is the reservoir 100 that is moved axially relative to the body 10 between a distal position, which is the rest position, and a proximal position. In the embodiment in the figures, the reservoir slides axially inside said inner sleeve 800.

The outlet orifice of the valve member 210 of said metering valve 200 is connected via a channel 300 to said mouthpiece 400 through which the user inhales the fluid to be dispensed. In known manner, said valve member 210 is received in a valve well 700 that defines said channel 300, at least in part. The valve well 700 may be formed integrally with the body 10, or, as in the embodiment shown, it may be formed by a part that is assembled on said body 10.

In the invention, the device includes an actuator 20. The actuator 20 is mounted, in particular force-fitted, on the end of the reservoir 100, and it includes a spring 21 that is adapted to be compressed when the user presses axially on said actuator 20. The spring 21 may be a conventional coil spring, as shown in particular in FIG. 10, or, in a variant, a plastics spring or a foam element, as can be seen in FIG. 11. The actuator 20 makes it possible to guarantee an actuation force for actuating the valve 200 that is well controlled, reproducible, and independent of the actuation force exerted by the user. It is always the compressed spring 21 that moves the reservoir 100 axially so as to actuate the valve 200. This makes it possible in particular to avoid any risk of jamming that could occur if the user exerts an actuation force that is too great.

Figure 10:
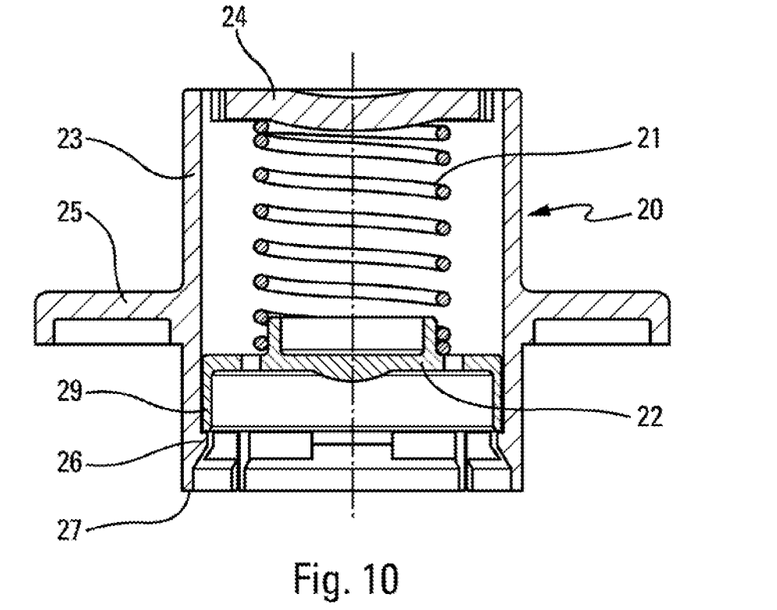
FIG. 10 is a diagrammatic section view of the FIG. 1 actuator.
Figure 11:
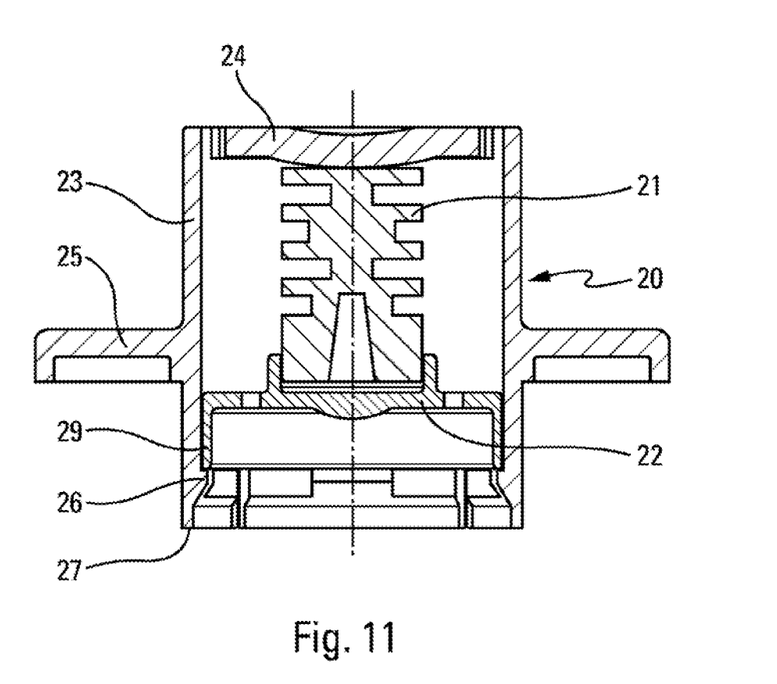
FIG. 11 is a view similar to the view in FIG. 10, showing a variant embodiment.

As can be seen in particular in FIGS. 10 and 11, the actuator 20 comprises a proximal wall 22 that is fastened, in particular force-fitted, on the end of the reservoir 100, and a body 23 that extends around said proximal wall 22 and slides axially past it, with the spring 21 arranged between said proximal wall 22 and a distal wall 24 of said body 23. Firstly, said body 23 slides axially past said proximal wall 22 between a rest position, shown in FIGS. 1, 10, and 11, and a cocked position, shown in FIGS. 2 and 5, in which said spring 21 is compressed as much as possible. Secondly, said body 23 slides axially past said proximal wall 22 between said cocked position and an actuated position, shown in FIG. 6, in which the spring 21 has transmitted its force, so as to move the reservoir 100 in the body 10, so as to actuate the valve 200.

Advantageously, the actuator 20 may include radial lugs 25 that extend radially outwards on either side of the body 23, making it easier for the user to press axially. Naturally, the radial lugs 25 are not essential, and the user can press axially on said distal wall 24 of the body 23.

In the embodiment shown in the figures, the rest position of the actuator 20 is advantageously defined by an axial abutment that is formed between a bottom axial edge 29 of said proximal wall 22 and an inner radial shoulder 26 of the body 23. The cocked position is advantageously defined by an axial abutment that is formed between a bottom axial edge 27 of the body 23 and a top axial edge 801 of the inner sleeve 800. In a variant, the axial abutment of the cocked position could also be formed with a top axial edge of the body 10.

The device includes a blocking element 500 that is movable and/or deformable between a non-actuation position in which said metering valve 200 cannot be actuated, and an actuation position in which said metering valve 200 can be actuated. In the rest position, said blocking element 500 is in its non-actuation position, and it is the user inhaling through the mouthpiece 400 that moves and/or deforms said blocking element 500 towards its actuation position. In other words, so long as the user does not inhale, it is impossible to actuate the metering valve 200, and it is only when the user inhales that said metering valve 200 can be actuated.

As described in greater detail below, the blocking element 500, in its non-actuation position, prevents the reservoir 100 from moving axially in the body 10. During inhaling, the blocking element 500 is moved and/or deformed so that it no longer prevents the reservoir 100 from moving axially in the body 10. Thus, after inhaling, such axial movement of the reservoir 300 causes the metering valve 200 to be actuated and a dose of fluid to be dispensed, synchronously with the inhaling.

Thus, in the absence of inhaling, there is no risk of an active dose of fluid being lost by accidental or incomplete actuation during which the user does not inhale. Actuating the valve 200 and expelling a dose of fluid are thus possible only when the user inhales and the reservoir 100 is moved simultaneously in the body 10 so as to actuate the valve 200.

The device includes a trigger system that is controlled by the user inhaling, and that is for moving and/or deforming said blocking element 500 from its non-actuation position towards its actuation position, when the user inhales through the mouthpiece 400.

The trigger system includes an inhalation-sensitive member 60 that is deformable and/or movable under the effect of inhaling, the inhalation-sensitive member 60 being adapted, when it is deformed and/or moved, to move and/or deform said blocking element 500 from its non-actuation position towards its actuation position.

As described in greater detail below, the inhalation-sensitive member 60 may be made in the form of a deformable air chamber, e.g. a bellows or a deformable pouch.

Advantageously, the non-actuation position corresponds to a position in which the reservoir 100 is blocked in the body 10. In this blocked position, the reservoir 100 is prevented from moving by said blocking element 500 that is released only at the moment of inhaling.

The blocking element 500 is advantageously formed by a blocking ring that includes at least one, and preferably three, axial blocking tabs 501 that are elastically deformable radially outwards. The blocking ring is fastened, in particular snap-fastened, on the reservoir 100, in particular on the cap 5 that fastens the metering valve 200 on the reservoir 100. In the rest position, said blocking tabs 501 bear against a radial shoulder 710 (as can be seen more clearly in FIGS. 4 and 7) of said valve well 700. The radial shoulder 710 preferably slopes downwards and radially outwards, forming an angle y with the longitudinal central axis X of the valve 200, such that when the reservoir 100 slides axially in the body 10 during actuation, said axial blocking tabs 501 slide over said sloping shoulder 710, thereby deforming them radially outwards.
Advantageously, the angle y is greater than 20°, preferably greater than 30°, and it is naturally less than 90°.

Figure 7:
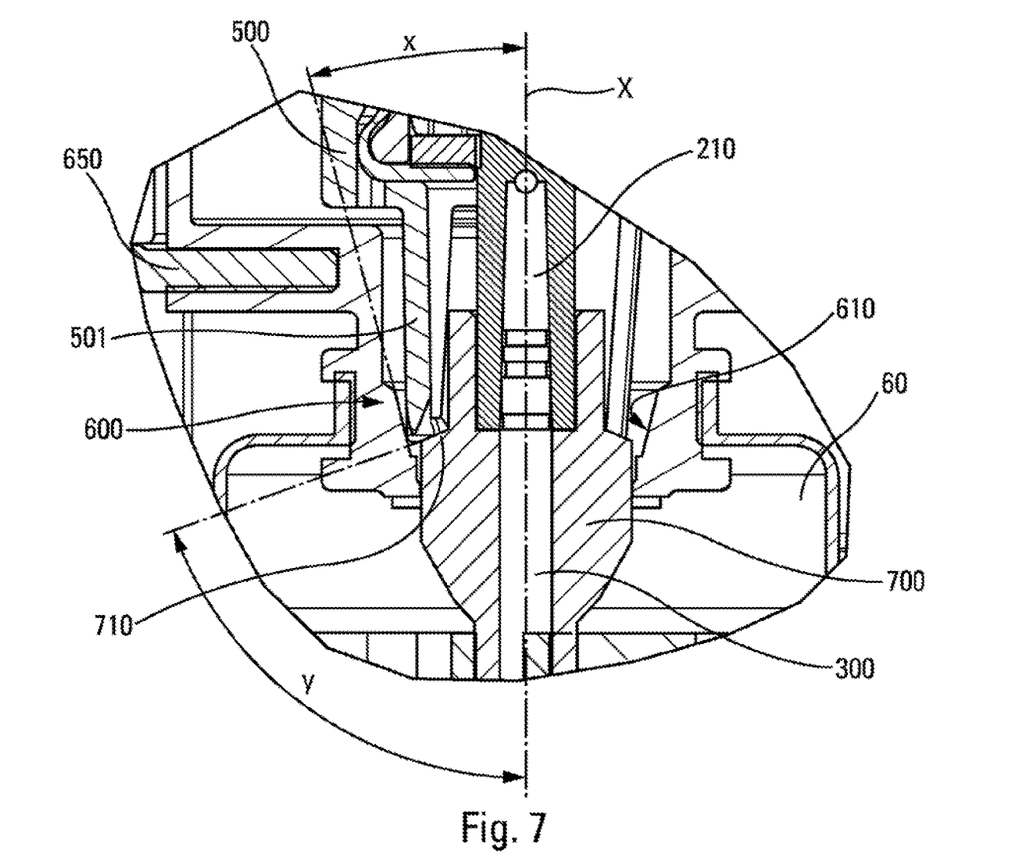
FIG. 7 is a larger-scale detail view of a portion of FIG. 1.
Figure 8:
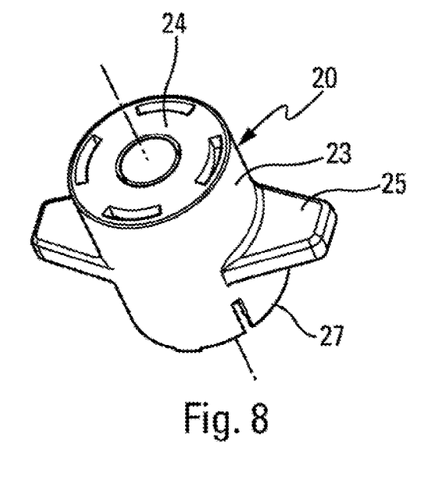
FIG. 8 is a diagrammatic perspective view of the FIG. 1 actuator.
Figure 9:
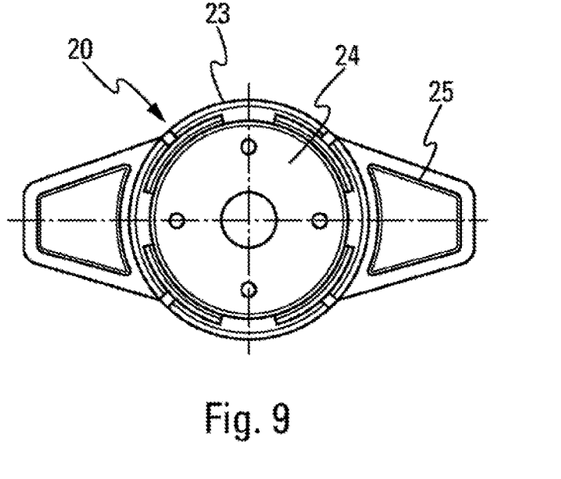
FIG. 9 is a diagrammatic plan view of the FIG. 1 actuator.

A trigger element 600 is mounted around said valve well 700 to slide axially between a blocking position in which it blocks said blocking element 500 in its non-actuation position, and a release position in which it no longer blocks said blocking element 500. In particular, said trigger element 600, in its blocking position, co-operates with said blocking tabs 501, preventing any deformation radially outwards of said blocking tabs 501. Thus, when said trigger element 600 is in its blocking position, it prevents said blocking tabs 501 from deforming radially outwards, which blocking tabs consequently remain blocked axially by said shoulder 710 of the valve well 700, thereby preventing the reservoir 100 from moving axially and the metering valve 200 from thus being actuated. Advantageously, the surface 610 of the trigger element 600 chat co-operates with said blocking tabs 501 in its blocking position, slopes and forms an angle x with the longitudinal central, axis X of the valve 200, as shown in FIG. 7. The angle x is advantageously less than 30°, preferably less than 15°.

In the specifications required, it is possible to optimize the angles x and y so as to make it easier to actuate the inhalation-controlled trigger system.

The trigger element 600 is connected to said inhalation-controlled trigger system, in particular to said inhalation-sensitive member 60, so that when said inhalation-sensitive member deforms and/or moves, it causes said trigger element 600 to pass from its blocking position towards its release position.

Figure 5:
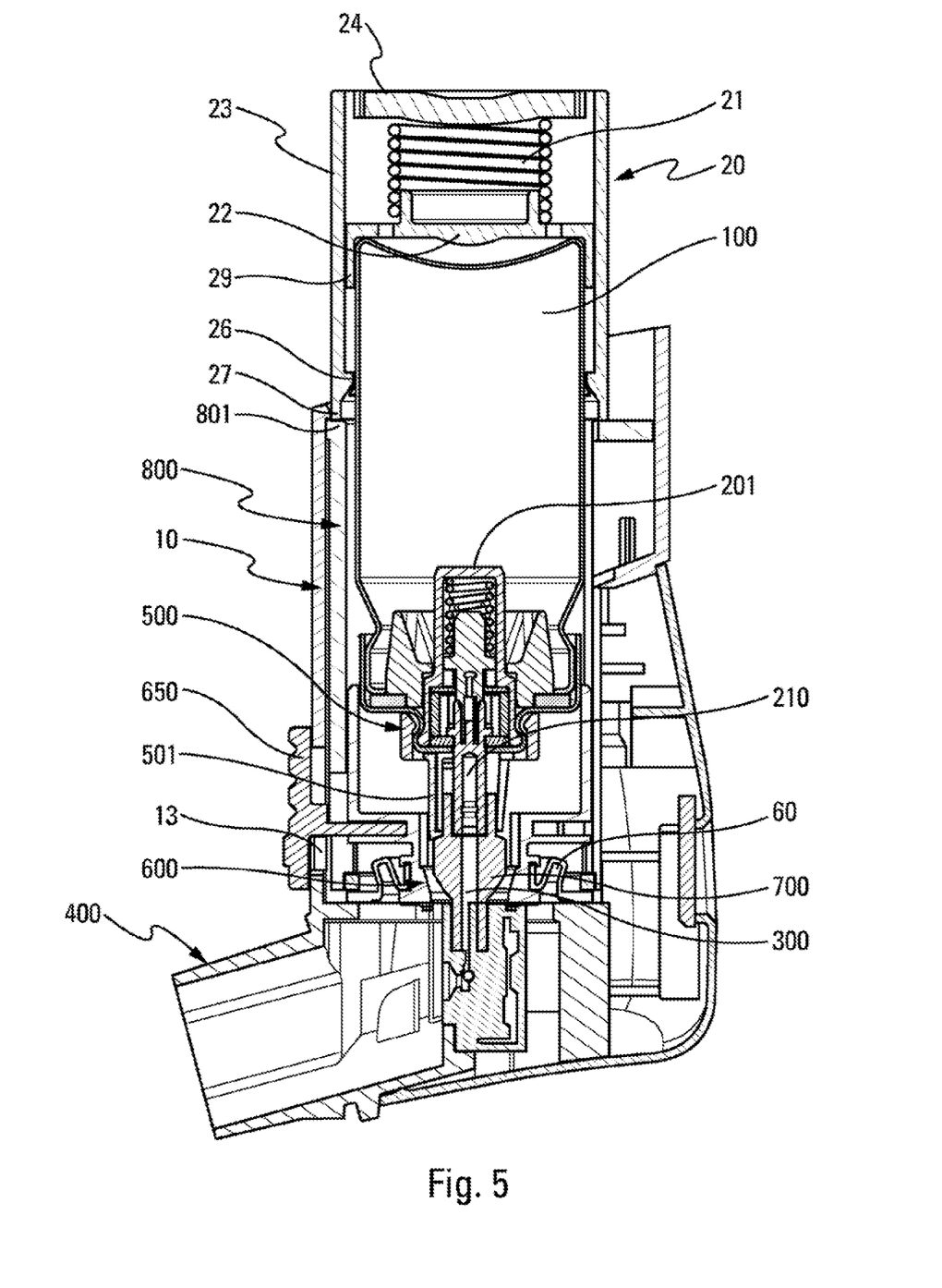
FIG. 5 is a view similar to the view in FIG. 2, shown in the position after suction.
Figure 6:
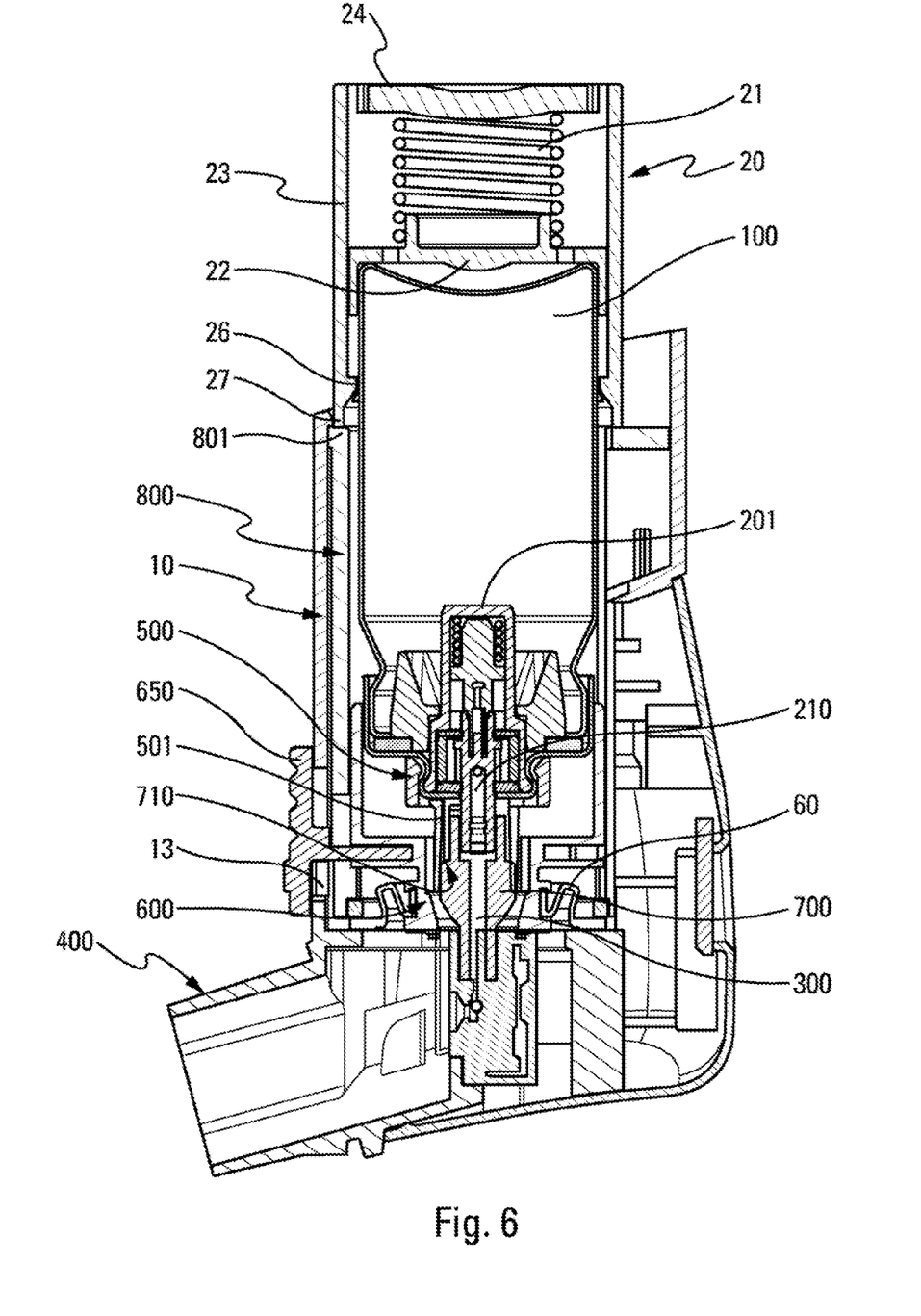
FIG. 6 is a view similar to the view in FIG. 5, shown in the position for dispensing a dose of fluid.

In its blocking position, the trigger element 600 advantageously co-operates in substantially airtight manner with the outside of the valve well 700, so as to use most of the inhalation flow to actuate the inhalation-controlled trigger system. When the trigger element 600 leaves its blocking position and moves towards its release position, it opens an air passage around said valve well, as can be seen in FIGS. 5 and 6. This facilitates inhaling by drawing in air, thereby improving dose-taking effectiveness. In addition, drawing air in this way makes the inhaling process more comfortable for the user.

The trigger element 600 is advantageously fastened to an outer sleeve 650 that forms a cover and that slides axially over the outside of the body 10. The cover 650 co-operates with an opening 13 for substantially opening the opening 13 in the blocking position, and for substantially closing the opening 13 in the release position. Since the opening 13 is open at the start of inhaling, it enables the inhalation trigger system, and in particular the inhalation-sensitive member 60, to be actuated reliably, by avoiding any suction outside said inhalation-sensitive member 60 when it deforms. This makes it possible to optimize such triggering by inhaling. When the trigger element 600 is moved axially towards its release position under the effect of inhaling, and thus when the metering valve 200 can be actuated so as to dispense a dose of fluid, the cover 650 closes the opening 13.

Advantageously, said cover 650 is accessible from the outside. This makes it possible, if necessary, to move the trigger element 600 manually, so as to be able to actuate the metering valve 200 even without inhaling, e.g. when the person that needs to receive the dose of fluid is incapable of inhaling sufficiently. This is thus a safety measure.

The inhalation-sensitive member 60 is advantageously made in the form of a deformable air chamber. Advantageously, the air chamber comprises a deformable membrane that is connected firstly to the body 10 and secondly to said trigger element 600.

During inhaling, the deformable membrane of the inhalation-sensitive member 60 deforms and/or contracts under the effect of the suction generated by inhaling, causing the trigger element 600 to move from its blocking position towards its release position. This then enables said blocking tabs 501 to deform radially, and thus enables said blocking element 500 to move from its non-actuation position towards its actuation position. The figures show a deformable membrane made in the form of a pouch or a diaphragm, but said membrane could be made in some other way, e.g. in the form of a bellows. Naturally, other forms can also be envisaged.

The valve 200 is thus actuated only at the moment of inhaling, such that the dose of fluid is expelled out of the dispenser orifice simultaneously with inhaling.

Figure 2:
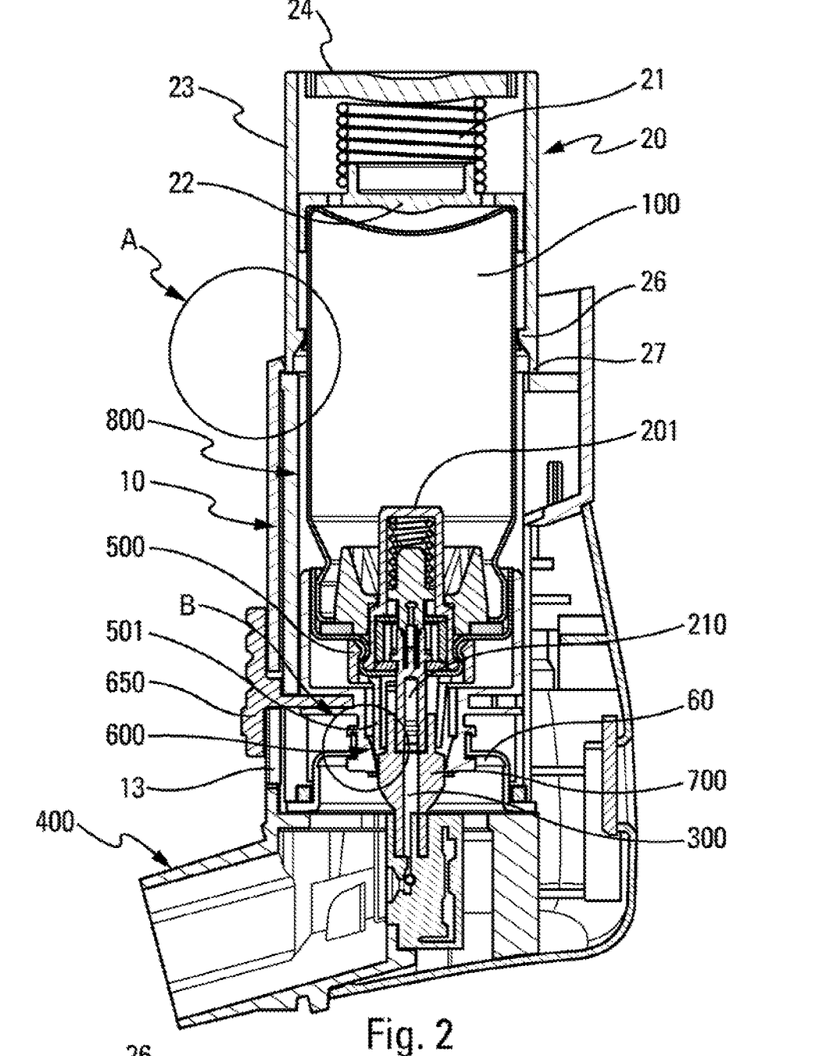
FIG. 2 is a view similar to the view in FIG. 1, shown in the non-dispensing position before suction.
Figure 3:
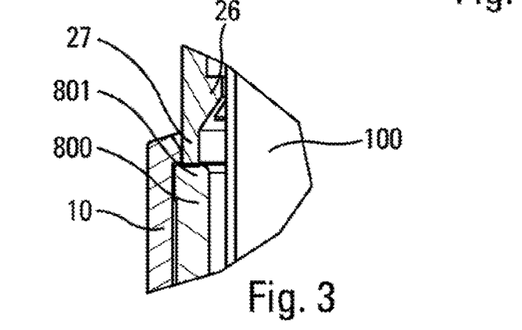
FIG. 3 is a larger-scale view of a detail A in FIG. 2.

When the user wishes to use the device, the user places the mouthpiece 400 in the mouth, and presses manually on the actuator 20. The actuator can thus slide axially past the reservoir 100 between its rest position and its cocked position so as to compress the spring 21, until the actuator 20 comes into abutment with the body 10, as can be seen in FIG. 2. The compressed spring 21 exerts an axial force on the reservoir 100 via said proximal wall 22, but said reservoir 100 is blocked and prevented from sliding in the body 10 by the blocking tabs 501 of the blocking element 500, which blocking tabs bear against the shoulder 710 of the valve well 700. Optionally, the reservoir 100 may perform an initial short axial stroke before becoming blocked, this initial short stroke however being insufficient to actuate the metering valve 200. FIG. 1 shows the device at rest, and FIG. 2 shows the device in the position with the reservoir 100 blocked, after the actuator 20 has been cocked and before inhaling.

Figure 4:
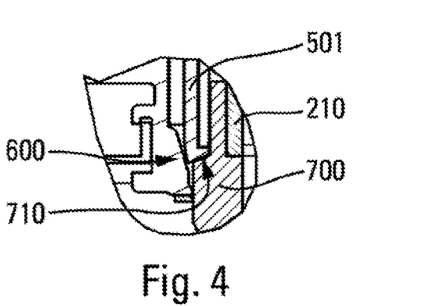
FIG. 4 is a larger-scale view of a detail B in FIG. 2.

When the user inhales through the mouthpiece 400, the inhalation-sensitive member 60 deforms, and this causes the trigger element 600 that is fastened to said inhalation-sensitive member 60 to slide, as can be seen in FIG. 4. The movement of the trigger element 600 over the valve well 700 releases the tabs 501 of the blocking element 500 radially. Under the effect of the axial force transmitted by the spring 21 of the actuator 20 to the reservoir 100, the axial tabs 501 are able to deform radially outwards, and thus pass over said shoulder 710, so as to enable the reservoir 100 to slide towards its dispensing position, and the valve 200 thus to be actuated. The dispensing position is shown in FIG. 6.

At the end of inhaling, the trigger element 600 is returned upwards by the springiness of the membrane of the inhalation-sensitive member 60. If necessary, the trigger element can also be returned manually to its rest position, by sliding the cover 650 axially upwards.

When the user releases the pressure on the actuator 20, the reservoir 100 returns towards the rest position under the effect of the return spring of the valve 200, and the valve member 210 of the metering valve simultaneously returns to the rest position, once again filling the valve chamber with a new dose of fluid. In parallel, the actuator 20 also returns to its rest position under the effect of the spring 21. The device is thus ready for another utilization.

It should be observed that with the actuator 20, the device can also be actuated correctly when the user inhales before pressing on the actuator. Nevertheless, in order to optimize the inhalation-synchronized dispensing of a dose, it is preferable for the actuator 20 to be in its cocked position when the user starts inhaling.

The present invention applies, in particular, to treating asthma attacks or chronic obstructive pulmonary disease (COPD), by using formulations of the following types: salbutamol, aclidinium, formoterol, tiotropium, budesonide, fluticasone, indacaterol, glycopyrronium, salmeterol, umeclidinium bromide, vilanterol, olodaterol, or striverdi, or any combination of these formulations.

The present invention is described above with reference to an advantageous embodiment, but naturally any modification could be applied thereto by the person skilled in the art, without going beyond the ambit of the present invention, as defined by the accompanying claims.

The invention claimed is:

1. An inhalation-synchronized fluid dispenser device comprising a device body provided with a mouthpiece, a fluid reservoir containing a fluid and a propellant gas being mounted to slide axially in said device body, a metering valve including a valve member being assembled on said reservoir for selectively dispensing the fluid, said device further comprising:
   a blocking element that is movable and/or deformable between a non-actuation position in which said metering valve cannot be actuated, and an actuation position in which said metering valve can be actuated, said blocking element, in its non-actuation position, co-operating firstly with the device body and secondly with the reservoir so as to prevent said reservoir from moving axially in the device body; and
   an inhalation-controlled trigger system including an inhalation-sensitive member that is deformable and/or movable under the effect of inhaling, wherein, when said inhalation-sensitive member, is deformed and/or moved, is configured to move and/or deform said blocking element from its non-actuation position towards its actuation position;
   said device includes an actuator that is fastened on said reservoir, said actuator comprising a proximal wall that is fastened on an end of the reservoir, an actuator body that slides axially past said proximal wall, and a spring that is arranged between said proximal wall and a distal wall of said actuator body, said actuator body sliding axially past said proximal wall between a rest position and a cocked position in which said spring is compressed, such that on said inhalation-controlled trigger system being actuated, said compressed spring moves said reservoir axially in said device body so as to actuate said metering valve; and
   wherein said blocking element is a blocking ring that is fastened on said reservoir, and that includes at least one axial tab co-operating with a shoulder that is secured to said device body so as to prevent said reservoir from moving axially in said device body.

2. A device according to claim 1, wherein said at least one axial tab is deformable radially outwards so as to pass from the non-actuation position towards the actuation position, a trigger element being provided so as to hold said at least one axial tab in the non-actuation position.

3. A device according to claim 2, wherein said trigger element is mounted to move between a blocking position in which it blocks said blocking element in its the non-actuation position, and a release position in which it does not block said blocking element.

4. A device according to claim 3, wherein said inhalation-sensitive member of said inhalation-controlled trigger system includes a deformable membrane that defines a deformable air chamber, said deformable membrane being fastened to said trigger element, said deformable membrane being deformed during inhaling, so that it moves said trigger element from its blocking position towards its release position.

5. A device according to claim 1, wherein said spring is a coil spring.

6. A device according to claim 1, wherein said spring is a plastics spring.

7. A device according to claim 1, wherein said spring is a foam element.

8. A device according to claim 1, wherein said the actuator includes a radial flange that extends radially outwards on either side of said actuator body.

9. A device according to claim 1, wherein the rest position of said actuator is defined by an axial abutment that is formed between a bottom axial edge of said proximal wall and an inner radial shoulder of said actuator body.

10. A device according to claim 1, wherein the cocked position of said actuator is defined by an axial abutment that is formed between a bottom axial edge of said actuator body and a top axial edge of an inner sleeve that is secured to said device body.

11. The device according to claim 1, wherein said proximal wall is force-fitted on the end of the reservoir.

12. The device according to claim 1, wherein said blocking ring is snap-fastened on said reservoir.

13. The device according to claim 1, wherein said blocking ring includes three axial tabs co-operating with the shoulder that is secured to said device body.

* * * * *